United States Patent [19]
Hirose et al.

[11] Patent Number: 5,723,650
[45] Date of Patent: Mar. 3, 1998

[54] CYCLOHEXANE TRICARBOXYLIC ACID DERIVATIVE AND METHOD FOR THE PREPARATION THEREOF

[75] Inventors: Takuji Hirose, Tsukuba; Kazuyuki Kasuga, Tsuchiura; Hideki Sugihara, Tsukuba; Yuichiro Himeda, Tsukuba; Zhen-He Wang, Tsukuba; Bruce Baldwin, Tsukuba, all of Japan

[73] Assignee: Japan as represented by Director General of Agency of Industrial Science and Technology, Tokyo, Japan

[21] Appl. No.: 600,737

[22] Filed: Feb. 13, 1996

[30] Foreign Application Priority Data

Feb. 27, 1995 [JP] Japan ................................ 7-038460

[51] Int. Cl.[6] ............................................ C07C 69/74
[52] U.S. Cl. ................................ 560/127; 562/509
[58] Field of Search .......................... 560/127; 562/509

[56] References Cited

PUBLICATIONS

Curran et al., J. Org. Chem., 1994, vol. 59, pp. 3522–3529.
Ikeura et al., Chemistry Letters, 1990, pp. 169–172.
Menger et al., J. Am. Chem. Soc., 1988, vo. 110, pp. 6794–6796 & Supplemental Material Page.

Primary Examiner—Brian M. Burn
Attorney, Agent, or Firm—Wenderoth, Lind & Ponack

[57] ABSTRACT

Disclosed is a novel compound having activity as an ionophore for ion transport, which is a monoester or monoamide of 1,3,5-trimethyl-1,3,5-cyclohexane tricarboxylic acid, i.e. Kemp's triacid or the stereoisomer thereof, the group R in the ester group —COOR or in the amide group —CONHR being an aralkyl group or aryloxyalkyl group having 7 to 20 carbon atoms. The monoester and monoamide derivatives can be synthesized from anhydride of Kemp's triacid by subjecting the anhydride to a ring-opening esterification or amidation reaction with an alcohol or amine. On the other hand, both of the stereoisomers can be obtained by the dehydrohalogenation reaction of 1,3,5-trimethyl-1,3,5-cyclohexane tricarboxylic acid anhydride acid halide with an alcohol or amine followed by the ring-opening hydrolysis reaction on the anhydride group.

9 Claims, 1 Drawing Sheet

FIGURE
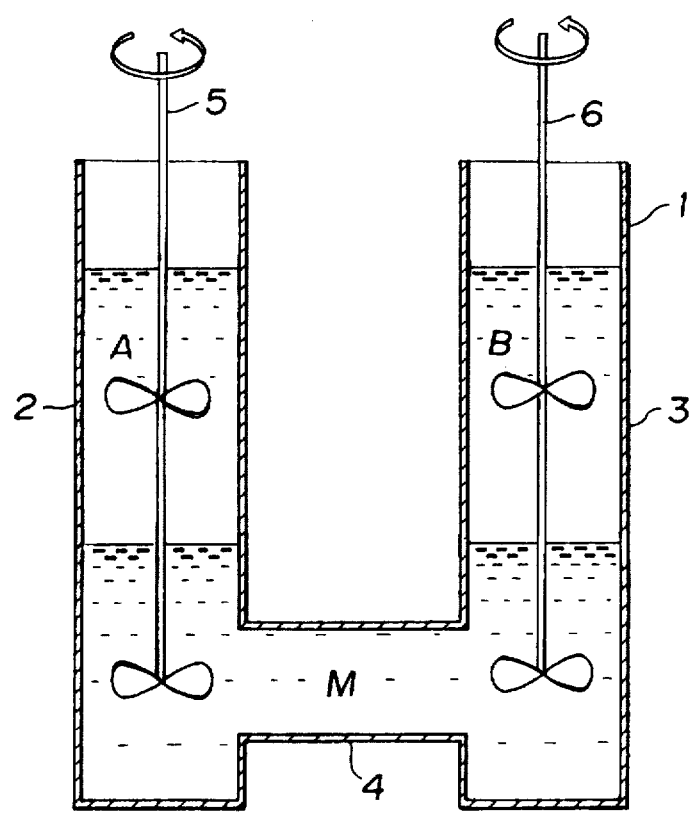

CYCLOHEXANE TRICARBOXYLIC ACID DERIVATIVE AND METHOD FOR THE PREPARATION THEREOF

BACKGROUND OF THE INVENTION

The present invention relates to a novel cyclohexane tricarboxylic acid derivative and a synthetic method for the preparation thereof. More particularly, the invention relates to a monoester or monoamide compound of cyclohexane tricarboxylic acid known in the name of Kemp's triacid and the stereoisomer thereof as well as an efficient synthetic method for the preparation of these novel compounds. The compounds are useful as an ionophore for transport of metal ions capable of selectively and continuously extracting specific metal ions from an aqueous solution containing various kinds of metal ions in combination.

One of the very important technological issues in recent years is to recover noble metals such as silver, gold and the like from wastes and to remove noxious metallic ingredients such as copper, lead, mercury and the like from an aqueous solution containing these metals in the form of metal ions from the standpoint of resource preservation and prevention of environmental pollution. The method as a major current heretofore for the separation of these metal ions from an aqueous solution utilizes adsorption of the metal ions onto an adsorbent such as ion exchange resins, active charcoal, metal-chelating agents and the like by bringing the aqueous solution into contact with the adsorbent. A method based on a novel principle of ion transport is recently under way of development in which the metal ions contained in an aqueous solution are selectively extracted and transported through a liquid film by means of an ion transport agent. This method is highlighted in respect of the expected high efficiency because a continuous process is applicable to the method.

Various kinds of ion transport agents, each of which serves to selectively capture a specific kind or more of metal ions, have been proposed heretofore including troponoid-adducts of a dithio crown ether compound and methionine derivatives having a 8-quinolyl group for mercury ions alone and cyclic polyether dicarboxylic acids for lead ions alone. The inventors also have proposed an α-amino acid diamide derivative as an ion transport agent to selectively capture copper ions alone (see, for example, Japanese Patent Kokai 5-163243).

On the other hand, so-called Kemp's triacid has been utilized in the studies on the phenomena of molecular recognition and self-replication (see Journal of American Chemical Society, volume 110, page 5192) but almost no attention has been directed to the relationship between this compound and metal ions.

SUMMARY OF THE INVENTION

The subject matters of the present invention, i.e. a novel cyclohexane tricarboxylic acid derivative and a method for the preparation thereof, have been unexpectedly discovered in the course of the investigations undertaken by the inventors with an object to develop a compound capable of serving as an ion transport agent with excellent selectivity for metal ions of plural kinds excepting alkali metal ions and exhibiting a high ion transport velocity.

Thus, the present invention provides a novel cyclohexane tricarboxylic acid derivative represented by the general planar structural formula

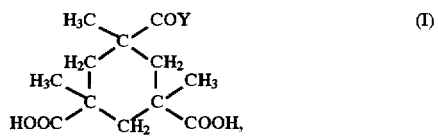

in which the symbol Y denotes a monovalent group represented by the formula —OR or —NHR, R being a monovalent hydrocarbon group or oxygen-containing monovalent hydrocarbon group.

While the above given formula (I) is a planar structural formula of the compound, there can be stereoisomers in connection with the stereospecific orientation of the group —COY relative to the cyclohexane ring. Namely, one of the stereoisomers, which is a derivative of Kemp's triacid, is represented by the stereostructural formula

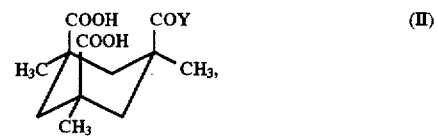

in which Y has the same meaning as defined above, and the other of the stereoisomers, which is a derivative of the stereoisomer of Kemp's triacid, is represented by the stereostructural formula

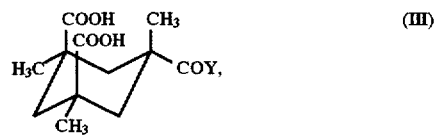

in which Y has the same meaning as defined above.

The above defined novel compound of the invention represented by the planar structural formula (I) can be prepared by mixing together cyclohexane tricarboxylic acid anhydride expressed by the formula

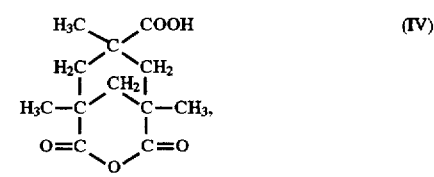

and a compound represented by the general formula

in which Y has the same meaning as defined above, so as to effect the ring-opening reaction on the anhydride group.

Alternatively, the compound of the planar structural formula (I) can be prepared by first mixing a cyclohexane tricarboxylic acid anhydride halide represented by the general formula

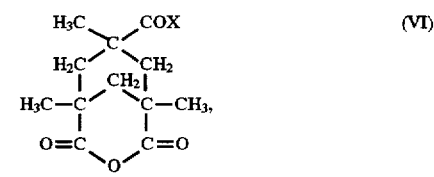

in which X is a halogen atom, and a compound of the general formula Y—H defined above in the presence of a dehydrohalogenating agent to effect a dehydrohalogenation reaction followed by a hydrolysis reaction to effect ring-opening of the anhydride group.

BRIEF DESCRIPTION OF THE DRAWING

The drawing is a FIGURE to schematically illustrate an apparatus for the ion transport experiments by using the inventive compound as an ionophore.

DETAILED DESCRIPTION OF THE PREFERRED EMBODIMENTS

The compound represented by the general formula (I) is a novel compound not known in the prior art nor reported in any literatures including the stereoisomer represented by the stereostructural formula (II), which is a monoester or monoamide of Kemp's triacid, and the stereoisomer represented by the stereostructural formula (III), which is a monoester or monoamide of the stereoisomer of Kemp's triacid.

In the above mentioned planar structural formula (I) and stereostructural formulas (II) and (III), the symbol Y denotes a monovalent group of the formula —OR or —NHR, in which R is a monovalent hydrocarbon group or an oxygen-containing monovalent hydrocarbon group. When the compound of the invention is to be used as an ion transport agent, it is preferable that the group denoted by R has from 7 to 20 carbon atoms including aralkyl groups and aryloxyalkyl groups in view of the decreased hydrophilicity of the compound imparted thereby.

Examples of the monovalent hydrocarbon group as R include alkyl groups such as propyl, butyl, hexyl, octyl, nonyl, decyl, dodecyl, tetradecyl, pentadecyl, octadecyl and eicosyl groups, aryl groups such as phenyl and naphthyl groups, aralkyl groups such as benzyl, phenethyl, phenylpropyl, phenylbutyl and phenylhexyl groups and alkaryl groups such as tolyl, xylyl, ethylphenyl, butylphenyl, hexylphenyl and decylphenyl groups.

Examples of the above mentioned oxygen-containing monovalent hydrocarbon groups include oxaalkyl groups such as 3-oxahexyl and 4-oxaoctyl groups and aryloxyalkyl groups such as phenoxyethyl, phenoxypropyl and phenoxybutyl groups as well as alkyl, aryl, aralkyl and aryloxyalkyl groups substituted by one or more of hydroxyl groups.

The compound of the invention represented by the general formula (I) can be prepared by the reaction of an acid anhydride compound expressed by the formula (IV) and an alcohol or amine of the general formula Y—H. The acid anhydride compound of the formula (IV) as one of the reactants in this reaction can be prepared, for example, by subjecting Kemp's triacid, i.e. cis,cis-1,3,5-trimethyl-1,3,5-cyclohexane tricarboxylic acid, expressed by the stereostructural formula

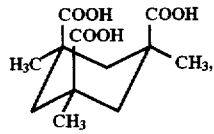

to a known procedure for the preparation of an anhydride compound such as heating under reduced pressure to effect dehydration and sublimation.

The reaction of the thus obtained Kemp's triacid anhydride and an alcohol or amine of the formula Y—H proceeds when these reactants are mixed together but it is advantageous that the reactants are dissolved in an appropriate organic solvent containing a basic compound and, optionally, a catalytic compound. Suitable organic solvents include aromatic hydrocarbon compounds such as benzene, toluene, xylene and the like, aliphatic and alicyclic hydrocarbon compounds such as n-hexane, n-heptane, cyclohexane and the like, halogenated hydrocarbon compounds such as methylene chloride, chloroform, ethylene chloride and the like and ether compounds such as dioxane, tetrahydrofuran and the like though not particularly limitative thereto. Methylene chloride is particularly preferred. The basic compound is preferably an organic base such as triethyl amine and the like. 4-Dimethylamino pyridine serves as a catalytic compound optionally used in the reaction.

Though dependent on the kind of the alcohol or amine as one of the reactants, use or non-use of a catalyst and other conditions, the reaction can proceed even at room temperature so that the reaction mixture is kept or heated at a temperature in the range from 0° to 100° C. or, preferably, from 10° to 60° C. Although the reaction takes place between equimolar amounts of the Kemp's triacid anhydride and the alcohol or amine compound, it is usually advantageous to use the alcohol or amine compound in an amount in slight excess over the stoichiometric amount relative to Kemp's triacid anhydride. The length of time required for completion of the reaction widely varies depending on various factors.

After completion of the reaction, the reaction mixture is washed with water and then subjected to the removal of the solvent and other volatile constituents by evaporation. The solid left after evaporation of the volatile constituents is subjected to recrystallization by using an appropriate solvent to give the desired product which is an acid monoester when the reactant Y—H is an alcohol compound and an acid monoamide when the reactant Y—H is an amine compound.

Alternatively to the above described synthetic method, the inventive compound can be prepared by another synthetic route in which the anhydride halide of the triacid represented by the general formula (VI) and the alcohol or amine compound of the general formula Y—H are subjected to a dehydrohalogenation reaction in the presence of a dehydrohalogenating agent followed by hydrolysis reaction to effect ring-opening of the anhydride ring. In the dehydrohalogenation reaction, the ring-opening reaction of the anhydride ring with the alcohol or amine compound may take place simultaneously but the reaction velocity thereof is much lower than that of the dehydrohalogenation reaction.

The anhydride halide of the triacid represented by the general formula (VI) as the reactant in this process can be prepared, for example, by the reaction of (1α,3α,5β)-1,3,5-trimethyl cyclohexane tricarboxylic acid, which is a stereoisomer of Kemp's triacid, with an acid halogenating agent such as thionyl chloride and the like.

The dehydrohalogenating agent used in the above mentioned dehydrohalogenation reaction is a basic compound which can be either an inorganic basic compound such as sodium carbonate, sodium hydrogencarbonate and the like or an organic basic compound such as triethyl amine, pyridine and the like. It is preferable to conduct the dehydrohalogenation reaction in an organic solvent which is selected from the group consisting of aromatic hydrocarbon compounds such as benzene, toluene, xylene and the like, aliphatic and alicyclic hydrocarbon compounds such as n-hexane, n-heptane, cyclohexane and the like, halogenated hydrocarbon compounds such as methylene chloride, chloroform, ethylene chloride and the like and ether compounds such as dioxane, tetrahydrofuran and the like though not particularly limitative thereto. Methylene chloride is particularly preferred.

Though dependent on the kind of the alcohol or amine compound as one of the reactants, kind of the dehydrohalogenating agent, use or non-use of a catalyst and other factors, the dehydrohalogenation reaction can proceed even at room temperature so that the reaction mixture is kept or heated at a temperature in the range from 0° to 100° C. or, preferably, from 10° to 60° C. The amount of the alcohol or amine compound used as one of the reactants can be substantially equimolar to that of the anhydride halide compound of the general formula (VI). The dehydrohalogenation reaction with an alcohol or amine is complete usually within 12 hours or within 1 hour, respectively.

After completion of the dehydrohalogenation reaction, the reaction mixture is thoroughly washed with water to remove water-soluble materials followed by the removal of volatile matter by evaporation to leave the stereoisomer of the Kemp's triacid anhydride ester or amide as a solid residue which is subjected to the subsequent hydrolysis reaction either as such or after purification by recrystallization from an appropriate solvent.

The above obtained acid anhydride ester or amide compound is then dissolved in an appropriate organic solvent and the solution is admixed with an aqueous solution of a basic compound such as lithium hydroxide, sodium hydroxide, potassium hydroxide and the like to effect hydrolysis of the acid anhydride ring. The organic solvent used here is exemplified by aromatic hydrocarbon compounds such as benzene, toluene, xylene and the like, aliphatic and alicyclic hydrocarbon compounds such as n-hexane, n-heptane, cyclohexane and the like, halogenated hydrocarbon compounds such as methylene chloride, chloroform, ethylene chloride and the like and ether compounds such as dioxane, tetrahydrofuran and the like, of which tetrahydrofuran is particularly preferable. The hydrolysis reaction is performed at a temperature in the range from 0° to 100° C. or, preferably, from 10° to 60° C. and the reaction is complete usually within 12 hours.

After completion of the hydrolysis reaction, the reaction mixture is subjected to an extraction treatment by using an appropriate solvent such as methylene chloride, ethyl acetate, chloroform and the like to give an extract from which the solvent is removed by evaporation leaving a solid material which is subjected to purification to give the desired product which is a diacid monoester, when the reactant Y—H is an alcohol compound, or a diacid monoamide, when the reactant Y—H is an amine compound.

As is indicated by the above given general formula (I), the compound of the invention has two carboxyl groups and a group having a heteroatom, e.g. nitrogen atom or oxygen atom, in a molecule so that the compound serves as an ion transport agent in a liquid-membrane system consisting of a solution A, a solution M and a solution B to selectively transport metal ions contained in the solution A to the solution B through the intermediate layer of the solution M and also serves as an extracting agent for the selective extraction of specific metal ions contained in an aqueous solution.

The test for the phenomenon of ion transport mentioned above by using the inventive compound of the general formula (I) as an ionophore is performed in principle by sandwiching a liquid membrane of a solution M containing the inventive compound with a first liquid layer of a solution A containing certain kinds of metal ions and a second liquid layer of a solution B to which the metal ions are to be transported. To be more particular, firstly, the intermediate liquid membrane or layer M is formed from an organic solvent capable of dissolving the inventive compound but immiscible with both of the solvents forming the liquid layers A and B. Secondly, the solutions A and B are indirectly contacted each with the other through an intervening compartment containing a solution of the inventive compound M and partitioned with partition membranes. Thirdly, the solutions A and B are indirectly contacted with intervention of a membrane of a porous material such as a polymer film or paper sheet impregnated with the inventive compound.

The FIGURE of the accompanying drawing is a schematic cross sectional illustration of an experimental apparatus to realize the phenomenon of ion transport by using the inventive compound. The principal part of the apparatus is a U-shaped tube 1 consisting of the lower connecting portion 4 containing a solution M of the inventive compound as an ionophore and two legs 2 and 3 containing a solution of metal ions A and a solution or solvent B to which the metal ions are to be transported, respectively. Stirrers 5 and 6 are inserted into the legs 2 and 3, respectively. It is of course essential that the solution M is substantially immiscible with either the solution A or the solution B and the solution M is heavier than each of the solutions A and B. To start the ion transport experiment, the solution M of the inventive compound is first introduced into the U-tube 1 to fill up the connecting part 4 and then the solutions A and B are each introduced into one of the legs 2 and 3, respectively.

The solution A contains the metal ions to be transported into the solution B. The solvent for the solution A is not limited to water but can be an organic solvent such as alcohols or a mixture of water and an organic solvent. It is preferable that the solution A is weakly alkaline or weakly acidic with a value of pH in the range from 3 to 9. The solution B which serves as a receptor of the metal ions from the solution A, on the other hand, is usually an acidic aqueous solution having a pH not higher than 3 containing an inorganic acid such as hydrochloric acid, sulfuric acid, nitric acid, phosphoric acid and the like or an organic acid such as formic acid, acetic acid, organic sulfonic acid and the like. The solution B optionally contains various kinds of cations which may be of the same kind as the metal ions to be transported thereinto.

In practicing the process of ion transport in the above described manner, it is possible that the concentration of the metal ions in the solution B is increased to exceed the concentration thereof in the starting solution A since the phenomenon of ion transport proceeds to counteract the concentration gradient of the metal ions. As is stated before, the solution M should be substantially immiscible with the solutions A and B so that, when the solutions A and B are each an aqueous solution, the solution M is prepared by using a water-immiscible solvent including hydrocarbon solvents such as benzene, toluene and the like, halogenated hydrocarbon solvents such as chloroform, carbon tetrachloride, dichloroethane and the like and water-immiscible higher alcohols such as hexyl alcohol, octyl alcohol and the like.

When the ion transport system is constructed in the above described fashion, the metal ions contained in the alkaline or weakly acidic solution A are transferred into the solution M and captured by the inventive compound while the metal ions contained in the solution M are released into the acidic solution B when the solution M is contacted with the solution B thus to result in the transport of the metal ions from the solution A to the solution B.

The efficiency of the ion transport process by using the inventive compound is very high for polyvalent metal ions such as ions of alkaline earth metals, copper, lead, zinc and the like though less efficient for monovalent metal ions such as ions of alkali metals. It is of course that the inventive compound serves as a selective extracting agent for metal ions.

As is described above, the novel compound disclosed by the present invention exhibits excellent selectivity in the phenomenon of ion transport so that the compound provides a means for the transfer of a specific kind of metal ions from a first solution A to a second solution B with a possibility to obtain the solution B containing the metal ions in a concentration higher than that in the solution A by counteracting the concentration gradient of the metal ions. By using the compound of the present invention as a selective transport agent of metal ions, an efficient means is provided for the selective and continuous separation of a specific kind of metal ions with a high efficiency from an aqueous solution containing various kinds of metal ions in combination. The compound of the present invention is useful also as a selective extracting agent for metal ions.

In the following, the present invention is described in more detail by way of examples, which, however, never limit the scope of the invention in any way.

EXAMPLE 1

Kemp's triacid monophenethyl ester was prepared in the following manner. Thus, 237 mg (1.94 mmoles) of phenethyl alcohol and a catalytic amount of 4-dimethylaminopyridine were added to 10 ml of a methylene chloride solution containing 424 mg (1.76 mmoles) of Kemp's triacid anhydride and 623 mg (6.16 mmoles) of triethylamine to be dissolved therein and the mixture was agitated overnight at room temperature to effect the ring-opening reaction of the acid anhydride. Thereafter, the reaction mixture was washed thrice each time with 30 ml of a 1M aqueous solution of citric acid followed by drying over anhydrous magnesium sulfate and then subjected to removal of the solvent and other volatile materials by evaporation to leave a solid material which was purified by recrystallization from benzene to give 368.7 mg of a colorless and transparent crystalline material having a melting point at 166.0° to 166.7° C. as a product. This product could be identified to be Kemp's triacid monophenethyl ester from the results of the analyses shown below. The above mentioned yield of the product corresponds to 57.9% of the theoretical value.

(1) Infrared absorption spectrum 1738 $cm^{-1}$ (C=O, ester); 1707 $cm^{-1}$ (C=O, acid); 1175 $cm^{-1}$ (C—O, ester); 748 $cm^{-1}$ (benzene); 698 $cm^{-1}$ (benzene)

(2) $^1$H-NMR spectrum (CDCl$_3$, δ, ppm) 7.25 (m, 5H); 4.17 (t, J=7.27 Hz, 2H); 2.95 (d, J=14.3 Hz, 2H); 2.94 (t, J=7.23 Hz, 2H); 2.59 (d, J=14.3 Hz, 1H); 1.20 (s, 6H); 1.15 (s, 3H); 0.996 (d, J=14.3 Hz, 1H); 0.905 (d, J=14.6 Hz, 2H)

(3) $^{13}$C-NMR spectrum (CDCl$_3$, δ, ppm) 182.4; 176.3; 138.4; 129.0; 128.2; 126.2; 65.0; 44.3; 42.0; 41.6; 41.1; 34.7; 33.1; 29.7

| (4) Elemental analysis | | |
|---|---|---|
| | C | H |
| Found, % | 66.09 | 7.22 |
| Calculated, %, for C$_{20}$H$_{26}$O$_6$ | 66.29 | 7.23 |

EXAMPLE 2

Mono(o-hydroxyphenoxypropyl) ester of Kemp's triacid was prepared in the following manner. Thus, 60.1 mg (0.36 mmole) of o-hydroxyphenoxypropyl alcohol and a catalytic amount of 4-dimethylaminopyridine were added to 2 ml of a methylene chloride solution containing 78 mg (0.33 mmole) of Kemp's triacid anhydride and 148 mg (7.46 mmoles) of triethylamine and dissolved therein followed by agitation of the thus obtained solution overnight at room temperature to effect the reaction. Thereafter, the reaction mixture was washed three times each with 6 ml of a 0.1M aqueous solution of citric acid followed by drying over anhydrous magnesium sulfate and removal of the solvent and volatile materials by evaporation to leave a white solid which was purified by recrystallization from acetonitrile to give 88.4 mg of an ivory white crystalline product having a melting point at 163.6° to 164.2° C. This product compound could be identified to be mono(o-hydroxyphenoxypropyl) ester of Kemp's triacid from the results of the analyses shown below. The above mentioned yield of the product corresponds to 66.6% of the theoretical value.

(1) Infrared absorption spectrum 3370 $cm^{-1}$ (O—H); 1709 $cm^{-1}$ (C=O, acid); 1304 $cm^{-1}$ (C—O, ester); 745 $cm^{-1}$ (benzene)

(2) $^1$H-NMR spectrum (acetone-D$_6$, δ, ppm) 6.80 (m, 4H); 4.16 (t, J=6.36 Hz, 2H); 4.11 (d, J=6.21 Hz, 2H); 2.72 (d, J=14.1 Hz, 3H); 2.11 (m, 2H); 1.26 (s, 6H); 1.22 (s, 3H); 1.19 (d, J=14.3 Hz, 3H)

(3) $^{13}$C-NMR spectrum (acetone-D$_6$, δ, ppm) 179.0; 177.3; 122.0; 120.4; 116.0; 113.6; 66.4; 62.0; 43.0; 42.2; 42.1; 31.6; 30.6; 29.1

| (4) Elemental analysis | | |
|---|---|---|
| | C | H |
| Found, % | 61.67 | 6.91 |
| Calculated, %, for C$_{21}$H$_{28}$O$_8$ | 61.76 | 6.91 |

EXAMPLE 3

Kemp's triacid monophenethylamide was prepared in the following manner. Thus, 277.4 mg (2.29 mmoles) of phenethylamine and a catalytic amount of 4-dimethylaminopyridine were added to 10 ml of a methylene chloride solution containing 500 mg (2.08 mmoles) of Kemp's triacid anhydride and 740 mg (7.28 mmoles) of triethylamine and dissolved therein followed by agitation of the thus obtained solution overnight at room temperature to effect the reaction. Thereafter, the reaction mixture was washed three times each with 30 ml of a 0.1M aqueous solution of citric acid followed by drying over anhydrous magnesium sulfate and removal of the solvent and volatile materials by evaporation to leave a white solid material which was purified by recrystallization from benzene to give 616.5 mg of a white crystalline product having a melting point at 245.2° to 246.8° C. This product compound could be identified to be Kemp's triacid monophenethylamide from the results of the analyses shown below. The above mentioned yield of the product corresponds to 82.0% of the theoretical value.

(1) Infrared absorption spectrum 3349 $cm^{-1}$ (N—H); 1717 $cm^{-1}$ (C=O, acid); 1682 $cm^{-1}$ (C=O, amide); 1190 $cm^{-1}$ (C—O)

(2) $^1$H-NMR spectrum (CDCl$_3$, δ, ppm) 8.57 (bs, 2H); 7.24 (m, 5H); 3.35 (m, 2H); 2.82 (m, 4H); 2.54 (d, J=12.7 Hz, 1H); 1.21 (s, 6H); 1.19 (s, 3H); 1.06 (d, J=14.3 Hz, 1H); 0.970 (d, J=15.4 Hz, 2H)

(3) $^{13}$C-NMR spectrum (CDCl$_3$-D$_6$, δ, ppm) 183.8; 177.5; 139.6; 128.8; 128.4; 126.2; 44.5; 42.7; 42.0; 41.6; 35.4; 29.5

| (4) Elemental analysis | | | |
|---|---|---|---|
|  | C | H | N |
| Found, % | 66.66 | 7.55 | 3.83 |
| Calculated, %, for $C_{20}H_{27}NO_5$ | 66.47 | 7.53 | 3.88 |

EXAMPLE 4

The stereoisomer of Kemp's triacid mono(p-n-butylanilide) was prepared in the following manner. Thus, 10 ml of a methylene chloride solution containing 243 mg (2.32 mmoles) of triethylamine and 126.9 mg (0.851 mmole) of p-n-butyl aniline were added to 10 ml of a methylene chloride solution containing 200 mg (0.773 mmole) of the acid anhydride chloride of ($1\alpha,3\alpha,5\beta$)-1,3,5-trimethyl cyclohexane tricarboxylic acid as a stereoisomer of Kemp's triacid and dissolved therein followed by agitation of the thus obtained solution overnight at room temperature to effect the reaction. Thereafter, the reaction mixture was washed thrice each with 25 ml of 1N hydrochloric acid and the organic solution was dried over anhydrous magnesium sulfate followed by removal of the solvent and volatile materials by evaporation to leave a white solid which was purified by recrystallization from benzene to give 217.5 mg of a colorless crystalline material which was assumed to be a stereoisomer of Kemp's triacid anhydride p-n-butylanilide. The above mentioned yield of this product corresponds to 76% of the theoretical value.

In the next place, 3 ml of a tetrahydrofuran solution containing 67.4 mg (0.181 mmole) of the above obtained product were admixed with 2 ml of an aqueous solution containing 16.7 mg (0.398 mmole) of hydrated lithium hydroxide and the mixture was agitated overnight at room temperature. The reaction mixture was extracted thrice each with 5 ml of chloroform and the extract as combined was dried over anhydrous magnesium sulfate followed by removal of the solvent and volatile materials by evaporation to give a solid material which was purified by recrystallization from benzene to give 21.1 mg of a colorless crystalline product having a melting point at 177.3° to 178.3° C. which could be identified to be the stereoisomer of Kemp's triacid mono(p-n-butylanilide) from the results of the analyses shown below. The above mentioned yield of the product corresponds to 30% of the theoretical value.

(1) infrared absorption spectrum 3283 $cm^{-1}$ (N—H); 1705 $cm^{-1}$ (C=O, acid); 1642 $cm^{-1}$ (C=O, amide)

(2) $^1$H-NMR spectrum ($CDCl_3$/acetone-$D_6$, $\delta$, ppm) 8.30 (s, 1H); 7.48 (d, J=8.43 Hz, 2H); 7.12 (d, J=8.52 Hz, 2H); 2.65 (d, J=14.6 Hz, 1H); 2.57 (t, J=7.67 Hz, 2H); 2.30 (d, J=14.5 Hz, 2H); 2.04 (d, J=14.5 Hz, 2H); 1.57 (m, 2H); 1.38 (m, 12H); 0.914 (t, J=7.31 Hz, 3H)

(3) $^{13}$C-NMR spectrum ($CDCl_3$/acetone-$D_6$, $\delta$, ppm) 181.7; 177.2; 139.0; 137.2; 129.3; 121.3; 43.6; 42.1; 41.6; 40.9; 35.7; 34.5; 30.4; 27.7; 22.9; 14.5

| (4) Elemental analysis | | | |
|---|---|---|---|
|  | C | H | N |
| Found, % | 67.66 | 8.02 | 3.60 |
| Calculated, %, for $C_{22}H_{31}NO_5$ | 67.85 | 8.02 | 3.60 |

EXAMPLE 5

An experiment of cation transport was undertaken for the Kemp's triacid monophenetyl ester prepared in Example 1 as an ionophore by using the apparatus illustrated in the FIGURE of the accompanying drawing.

In the first place, three solutions were prepared including, first, 15 ml of an aqueous solution, referred to as the solution A hereinafter, containing copper acetate, lead acetate, cobalt acetate and zinc acetate each in a concentration of 10 mM and having a pH of 6.2, second, 15 ml of a 0.1N aqueous solution of nitric acid, referred to as the solution B hereinafter, and, third, an organic solution, referred to as the solution M hereinafter, by dissolving 0.15 mmole of the ionophore compound in 30 ml of chloroform.

In the next place, the solution M was introduced into the apparatus 1 illustrated in the FIGURE to serve as the intermediate liquid layer and then the solutions A and B were introduced into the legs 2 and 3, respectively, of the apparatus 1. After standing of the apparatus 1 under gentle agitation at 25° C. for 48 hours with the stirrers 5 and 6, the solution B was analyzed by the atomic absorption spectroscopy to determine the amounts of the respective metal ions and to calculate the percentages of the metal ions transported from the solution A to the solution B through the intermediate layer of the solution M based on the amount of the metal ions initially contained in the solution A. The results are shown in Table 1 below.

TABLE 1

| Metal ions | $Cu^{2+}$ | $Pb^{2+}$ | $Ni^{2+}$ | $Co^{2+}$ | $Zn^{2+}$ |
|---|---|---|---|---|---|
| Amount of metal ions transported, µmoles | 85 | 150 | 2 | 0 | 33 |
| Percentage of metal ions transported | 57 | 100 | 1 | 0 | 22 |

As is understood from these results, the phenomenon of ion transport was selective for the divalent ions of lead, copper and zinc with this ionophore compound.

EXAMPLE 6

The experimental procedure for the ion transport test was just the same as in Example 5 excepting the use of Kemp's triacid monophenethylamide prepared in Example 3 as the ionophore compound in place of the Kemp's triacid monophenethyl ester. The amounts and percentages of the respective metal ions transported are shown in Table 2 below.

TABLE 2

| Metal ions | $Cu^{2+}$ | $Pb^{2+}$ | $Ni^{2+}$ | $Co^{2+}$ | $Zn^{2+}$ |
|---|---|---|---|---|---|
| Amount of metal ions transported, µmoles | 144 | 149 | 4 | 7 | 80 |
| Percentage of metal ions transported | 96 | 99 | 3 | 5 | 54 |

As is understood from these results, the phenomenon of ion transport was selective for the divalent ions of lead, copper and zinc with this ionophore compound.

EXAMPLE 7

The experimental procedure was about the same as in Example 5 excepting replacement of the solution A with 15 ml of another aqueous solution containing copper acetate and lead acetate each in a concentration of 10 mM and having a pH of 6.2 and the concentrations of copper ions and lead ions in the solution B were determined after 4 hours, 8 hours, 12 hours, 24 hours and 30 hours. The results of this cation transport experiment are shown in Table 3 below.

TABLE 3

| Lapse of time, hours | 4 | 8 | 12 | 24 | 30 |
| --- | --- | --- | --- | --- | --- |
| Amount of Cu²⁺ transported, μmoles | 14 | 36 | 57 | 92 | 105 |
| Percentage of Cu²⁺ transported | 9 | 24 | 38 | 61 | 70 |
| Amount of Pb²⁺ transported, μmoles | 77 | 129 | 142 | 149 | 150 |
| Percentage of Pb²⁺ transported | 51 | 86 | 95 | 99 | 100 |

EXAMPLE 8

The experimental procedure was the same as in Example 7 excepting replacement of the monophenethyl ester of Kemp's triacid with the same molar amount of the monophenethylamide of Kemp's triacid prepared in Example 3. The results of this cation transport experiment are shown in Table 4 below.

TABLE 4

| Lapse of time, hours | 4 | 8 | 12 | 24 | 30 |
| --- | --- | --- | --- | --- | --- |
| Amount of Cu²⁺ transported, μmoles | 34 | 76 | 106 | 138 | 145 |
| Percentage of Cu²⁺ transported | 23 | 51 | 71 | 92 | 97 |
| Amount of Pb²⁺ transported, μmoles | 48 | 98 | 128 | 146 | 149 |
| Percentage of Pb²⁺ transported | 32 | 65 | 86 | 98 | 99 |

EXAMPLES 9 TO 12

The experimental procedure in each of Examples 9, 10, 11 and 12 was substantially the same as in Example 5 except that the solution A was replaced with 15 ml of another aqueous solution containing magnesium chloride, calcium chloride, strontium chloride and barium chloride in combination each in a concentration of 10 mM and having a pH of 9.0 and that the ionophore compound contained in the solution M was the monophenethyl ester of Kemp's triacid prepared in Example 1, the mono(o-hydroxyphenoxypropyl) ester of Kemp's triacid prepared in Example 2, the monophenethylamide of Kemp's triacid prepared in Example 3 or the stereoisomer of the mono(p-n-butylanilide) of Kemp's triacid prepared in Example 4, respectively. The results of these cation transport experiments are shown in Table 5 below.

TABLE 5

| | Metal ions | Mg²⁺ | Ca²⁺ | Sr²⁺ | Ba²⁺ |
| --- | --- | --- | --- | --- | --- |
| Example 9 | Amount of metal ions transported, μmoles | 4 | 100 | 95 | 137 |
| | Percentage of metal ions transported | 3 | 67 | 63 | 91 |
| Example 10 | Amount of metal ions transported, μmoles | 2 | 103 | 79 | 130 |
| | Percentage of metal ions transported | 1 | 69 | 53 | 87 |
| Example 11 | Amount of metal ions transported, μmoles | 3 | 107 | 82 | 36 |
| | Percentage of metal ions transported | 2 | 72 | 55 | 24 |
| Example 12 | Amount of metal ions transported, μmoles | 4 | 120 | 94 | 32 |
| | Percentage of metal ions transported | 3 | 80 | 63 | 21 |

What is claimed is:

1. A monoester of 1,3,5-trimethyl-1,3,5-cyclohexane tricarboxylic acid represented by the formula

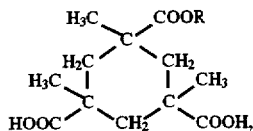

in which R is a an aralkyl group or aryloxyalkyl group having from 7 to 20 carbon atoms.

2. A monoamide of 1,3,5-trimethyl-1,3,5-cyclohexane tricarboxylic acid represented by the formula

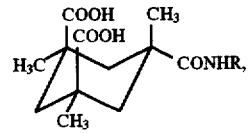

in which R is a monovalent hydrocarbon group or an oxygen-containing monovalent hydrocarbon group.

3. The monoester of 1,3,5-trimethyl-1,3,5-cyclohexane tricarboxylic acid as claimed in claim 1 which has a stereoisomeric structure represented by the formula

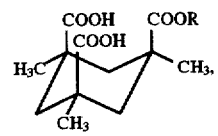

in which R has the same meaning as defined above.

4. The monoamide of 1,3,5-trimethyl-1,3,5-cyclohexane tricarboxylic acid as claimed in claim 2 which has a stereoisomeric structure represented by the formula

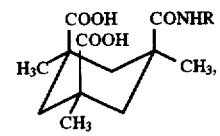

in which R has the same meaning as defined above.

5. The monoester of 1,3,5-trimethyl-1,3,5-cyclohexane tricarboxylic acid as claimed in claim 1 which has a stereoisomeric structure represented by the formula

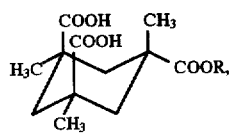

in which R has the same meaning as defined above.

6. The monoamide compound as claimed in claim 2 in which R is an aralkyl group or aryloxyalkyl group having from 7 to 20 carbon atoms.

7. The monoester compound as claimed in claim 1 in which R is an alkaryl group having from 7 to 20 carbon atoms.

8. The monoamide compound as claimed in claim 2 in which R is an alkaryl group having from 7 to 20 carbon atoms.

9. A method for the preparation of a monoester or monoamide compound of of 1,3,5-trimethyl-1,3,5-cyclohexane tricarboxylic acid represented by the formula

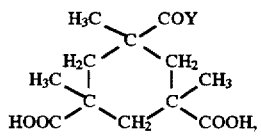

in which Y is a group of the formula —OR or —NHR, R being a monovalent hydrocarbon group or an oxygen-containing monovalent hydrocarbon group, which comprises the steps of:

(a) mixing a 1,3,5-trimethyl-1,3,5-cyclohexane tricarboxylic acid anhydride halide represented by the formula

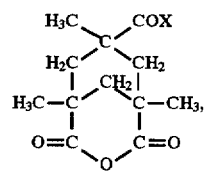

in which X is an atom of halogen, and a compound represented by the formula

Y—H, in which Y has the same meaning as defined above, in the presence of a dehydrohalogenating agent to give a dehydrohalogenation product; and (b) subjecting the dehydrohalogenation product obtained in step (a) to a hydrolysis reaction on the acid anhydride group.

* * * * *